United States Patent
Bauer et al.

(10) Patent No.: US 12,280,338 B2
(45) Date of Patent: Apr. 22, 2025

(54) ON-LINE DRYING OF HOLLOW FIBER MEMBRANES

(71) Applicant: GAMBRO LUNDIA AB, Lund (SE)

(72) Inventors: Ulrich Bauer, Hechingen (DE);
Reinhold Buck, Alleshausen (DE);
Juergen Graf, Dormettingen (DE);
Helmut Hildwein, Voehringen (DE);
Bernd Krause, Rangendingen (DE);
Markus Storr, Filderstadt (DE); Arnd Wochner, Dotternhausen (DE)

(73) Assignee: GAMBRO LUNDIA AB, Lund (SE)

( * ) Notice: Subject to any disclaimer, the term of this patent is extended or adjusted under 35 U.S.C. 154(b) by 37 days.

(21) Appl. No.: 17/483,929

(22) Filed: Sep. 24, 2021

(65) Prior Publication Data

US 2022/0023803 A1    Jan. 27, 2022

Related U.S. Application Data

(62) Division of application No. 15/538,533, filed as application No. PCT/EP2015/080754 on Dec. 21, 2015, now Pat. No. 11,154,820.

(30) Foreign Application Priority Data

Dec. 22, 2014  (EP) .................................... 14199664

(51) Int. Cl.
*B01D 67/00* (2006.01)
*A61M 1/16* (2006.01)
(Continued)

(52) U.S. Cl.
CPC ........... *B01D 67/0095* (2013.01); *A61M 1/16* (2013.01); *A61M 1/34* (2013.01); *B01D 67/0083* (2013.01);
(Continued)

(58) Field of Classification Search
None
See application file for complete search history.

(56) References Cited

U.S. PATENT DOCUMENTS 2,468,585 A    4/1949   Bluma
4,194,872 A *  3/1980   Hinterkeuser .......... B29C 48/05
                                                     425/327
(Continued)

FOREIGN PATENT DOCUMENTS

EP    0359636 A2    3/1990
EP    2591847 A1    5/2013
(Continued)

OTHER PUBLICATIONS

English translation of KR1020120054026.*
(Continued)

*Primary Examiner* — Jason Lau
(74) *Attorney, Agent, or Firm* — Barnes & Thornburg LLP

(57) ABSTRACT

The present invention relates to a continuous process for preparing permselective hollow fiber membranes being suitable e.g. for hemodialysis, hemodiafiltration and hemofiltration of blood which comprises a two-stage drying and tempering treatment of the hollow fiber membranes. According to a further aspect, the invention relates to a continuous process for drying permselective hollow fiber membranes on-line. The invention also relates to devices for on-line drying of permselective hollow fiber membranes.

17 Claims, 2 Drawing Sheets

(51) Int. Cl.
  *A61M 1/34* (2006.01)
  *B01D 69/08* (2006.01)
  *B01D 71/68* (2006.01)
  *D02J 13/00* (2006.01)

(52) U.S. Cl.
  CPC ....... *B01D 69/0871* (2022.08); *B01D 69/088* (2013.01); *B01D 71/68* (2013.01); *D02J 13/005* (2013.01); *A61M 2207/10* (2013.01); *B01D 2323/081* (2022.08); *B01D 2323/42* (2013.01); *B01D 2323/50* (2013.01)

(56) References Cited

U.S. PATENT DOCUMENTS

| | | | |
|---|---|---|---|
| 4,500,278 A | | 2/1985 | Cochran et al. |
| 4,738,035 A | * | 4/1988 | Grebe ................... F26B 13/08 34/631 |
| 4,902,456 A | | 2/1990 | Yen et al. |
| 2003/0209486 A1 | | 11/2003 | Kools |
| 2004/0232067 A1 | | 11/2004 | Simon |
| 2005/0176330 A1 | * | 8/2005 | Hama ................... B32B 27/281 442/411 |
| 2012/0097612 A1 | | 4/2012 | Nemser et al. |
| 2013/0118981 A1 | | 5/2013 | Vogel et al. |
| 2015/0075027 A1 | | 3/2015 | Maehara et al. |
| 2017/0368507 A1 | | 12/2017 | Bauer et al. |

FOREIGN PATENT DOCUMENTS

| | | | |
|---|---|---|---|
| JP | S6078604 A | | 5/1985 |
| JP | S61146306 A | | 7/1986 |
| JP | 2002363820 A | * | 12/2002 |
| KR | 1020120054026 | * | 5/2012 |
| WO | 2013/034611 A1 | | 3/2013 |
| WO | 2013/137237 A1 | | 9/2013 |

OTHER PUBLICATIONS

International Search Report and Written Opinion prepared for PCT/EP2015/080754, mailed Mar. 30, 2016, 13 pages.

Extended European Search Report, European Application No. 14199664.5, dated Jun. 17, 2015, 9 pages.

* cited by examiner

ON-LINE DRYING OF HOLLOW FIBER MEMBRANES

CROSS-REFERENCE TO RELATED APPLICATIONS

This application is a divisional application of U.S. patent application Ser. No. 15/538,533, filed on Jun. 21, 2017, which is the U.S. national stage entry of PCT International Application Number PCT/EP2015/080754, filed Dec. 21, 2015, which claims priority to European Patent Application Number 14199664.5, filed Dec. 22, 2014, the entire disclosures of all which are expressly incorporated by reference herein.

TECHNICAL FIELD

The present invention relates to a continuous process for preparing permselective hollow fiber membranes being suitable e.g. for hemodialysis, hemodiafiltration and hemofiltration of blood which comprises a two-stage drying and tempering treatment of the hollow fiber membranes. According to a further aspect, the invention relates to a continuous process for drying permselective hollow fiber membranes on-line. The invention also relates to devices for on-line drying of permselective hollow fiber membranes.

BACKGROUND OF THE INVENTION

The production process of permselective hollow fiber membranes usually involves a step of drying the membranes before they can be transferred into a housing to manufacture a filter. Drying can be effected discontinuously, e.g., by preparing membrane strands or bundles and subsequently drying them in drying chambers or ovens, or continuously, i.e., on-line. The majority of on-line drying processes known in the prior art involve drying the hollow fiber membranes with hot air, e.g., in convection ovens.

EP 2591847 A1 discloses a particular device for continuous drying of hollow fiber membranes with a drying gas.

JP 61/146306 A discloses a process for the production of a cellulosic hollow fiber membrane which involves contacting the membrane with a heated body. The preferred temperature of the heated body is 100 to 140° C.

WO 2013/034611 A1 discloses a process for the production of permselective hollow fiber membranes from a graft copolymer of polysulfone or polyethersulfone and polyvinylpyrrolidone which involves a drying step of the hollow fiber membrane. The drying step is performed a temperatures in the range of from 150° C. to 280° C. and can be performed as a continuous process, i.e. an online-drying process. Drying is performed in a single process step and no particulars of the drying time are given.

US 2015/0075027 A1 discloses a method for producing a porous membrane including a heating step comprising a water reduction step and a final drying step. In the water reduction step, a heating medium having a temperature $t_{gh}$ higher than the heat deformation temperature $T_d$ of the membrane material is used; in the final drying step, a heating medium having a temperature $t_{gh}$ not exceeding the heat deformation temperature $T_d$ of the membrane material is used. Temperatures $t_{gh}$ of 170° C. or higher are taught for the water reduction step; temperatures $t_{gh}$ of 120° C. or lower are recited for the final drying step. Superheated vapor, hot air or hot gas is used as heating medium. The reference also discloses a drying device comprising a water reduction unit and a final drying unit located downstream of the water reduction unit.

SUMMARY OF THE INVENTION

The present disclosure relates to a continuous process for preparing permselective hollow fiber membranes which comprises a two-stage drying and tempering treatment of the hollow fiber membranes. The two-stage drying and tempering treatment results in a narrow pore size distribution and high selectivity of the final membranes. The present disclosure also relates to devices for on-line drying of permselective hollow fiber membranes which are capable of performing the two-stage drying and tempering treatment. The devices comprise a plurality of rollers having a hot surface.

DETAILED DESCRIPTION

Figure 1:
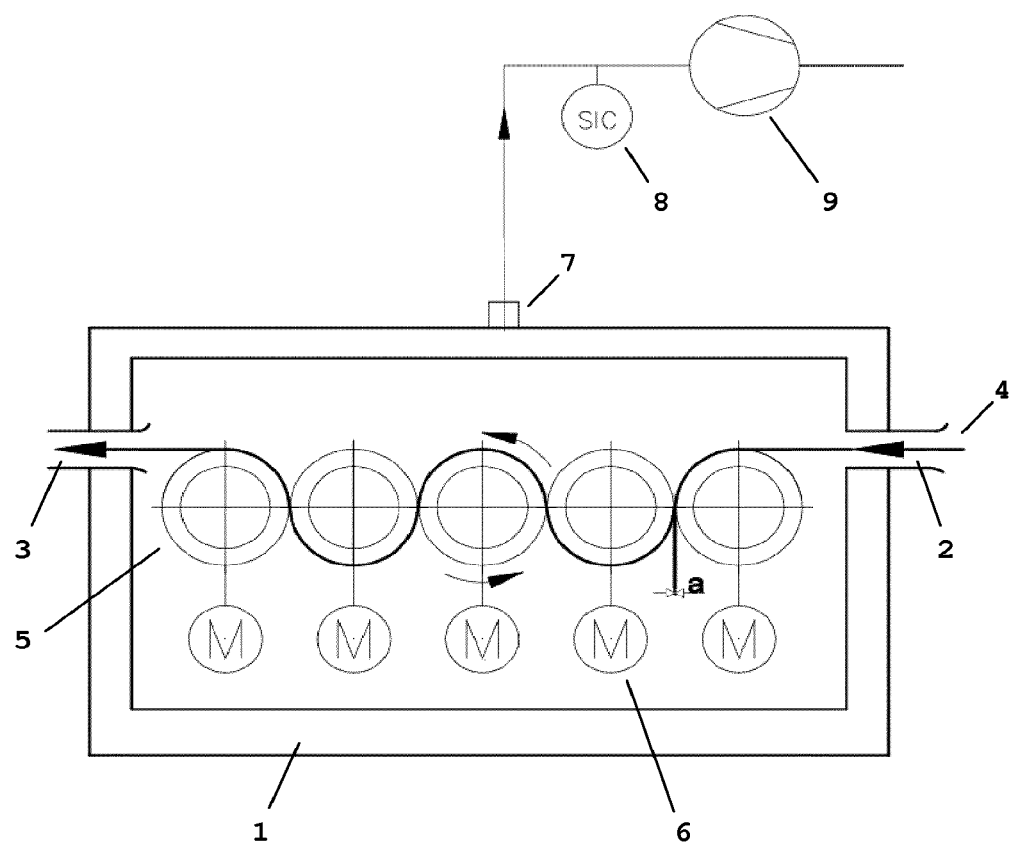
FIG. 1 shows a device according to an embodiment of the present disclosure.

The process of the present disclosure comprises the steps of continuously
a) extruding a polymer solution comprising
   i. at least one polysulfone, polyethersulfone (PES), or polyarylethersulfone (PAES), optionally in combination with polyamide (PA);
   ii. at least one polyvinylpyrrolidone (PVP); and
   iii. at least one solvent;
   through an outer ring slit of a nozzle with two concentric openings into a precipitation bath; simultaneously
b) extruding a center fluid through the inner opening of the nozzle;
c) washing the hollow fiber membrane obtained;
d) subjecting the hollow fiber membrane to a two-stage drying and tempering treatment;
wherein the two-stage drying and tempering treatment comprises drying the hollow fiber membrane by applying a temperature in the range of from 210 to 280° C., e.g., 220 to 260° C., to the outer surface of the hollow fiber membranes for a time in the range of from 1 to 4 seconds, e.g., 2 to 3 seconds; and subsequently tempering the hollow fiber membrane by applying a temperature in the range of from 180 to 200° C., to the outer surface of the hollow fiber membranes for a time in the range of from 2 to 5 seconds, e.g., 3 to 4 seconds.

The two-stage drying and tempering treatment provides for adequate evaporation of water and a defined shrinkage of pores. In one embodiment of the process, drying and tempering are effected by contacting the hollow fiber membrane with hot surfaces (e.g., heated rollers) having a temperature in the range of from 180 to 280° C.

Without wishing to be bound by theory, it is believed that by combining drying with additional tempering and by selecting the particular ranges for temperature and residence time, the pore structure of the freshly spun hollow fiber membrane is modified towards a narrower pore size distribution, resulting in higher selectivity of the final hollow fiber membrane.

The polymer solution which is used in step a) ("the spinning solution") comprises at least one polysulfone, polyethersulfone (PES), or polyarylethersulfone (PAES), optionally in combination with polyamide (PA); and at least one polyvinylpyrrolidone (PVP). In one embodiment, a polyvinylpyrrolidone which consists of a low molecular weight component having a molecular weight of below 100 kDa and a high molecular weight component having a molecular weight of 100 kDa or more is used for preparing the membrane.

An example of a suitable polyethersulfone is a polymer having the general formula —[O-Ph-$SO_2$-Ph-]$_n$-, a weight average molecular weight of about 60,000 to 65,000 Da, preferably 63,000 to 65,000 Da, and an Mw/Mn of about 1.5 to 1.8.

In one embodiment of the process, the polymer solution comprises from 12 to 16 wt %, related to the total weight of the solution, of polyethersulfone and from 3 to 12 wt %, e.g. 5 to 8 wt %, related to the total weight of the solution, of PVP, wherein said PVP consists of 3 to 8 wt %, e.g. 4 to 6 wt %, related to the total weight of the solution, of a low molecular weight (<100 kDa) PVP component and 0 to 4 wt %, e.g. 1 to 3 wt %, related to the total weight of the solution, of a high molecular weight (≥100 kDa) PVP component. In one embodiment, the total PVP contained in the spinning solution consists of from 22 to 34 wt %, e.g., from 25 to 30 wt % of a high molecular weight (≥100 kDa) component and from 66 to 78 wt %, e.g., from 70 to 75 wt % of a low molecular weight (<100 kDa) component. Examples for high and low molecular weight PVP are, for example, PVP K85/K90 and PVP K30, respectively.

In a particular embodiment, the polymer solution further comprises 66-81 wt % of solvent, related to the total weight of the solution, and 0-10 wt %, e.g. 0-5 wt %, related to the total weight of the solution, of suitable additives. Suitable additives are, for example, chosen form the group consisting of water, glycerol, and other alcohols. In one embodiment, water is present in the spinning solution in an amount of from 0 to 8 wt %, e.g., in an amount of from 2 to 6 wt %, related to the total weight of the solution.

In one embodiment, the solvent used in the process is chosen from the group consisting of N-methylpyrrolidone (NMP), N-ethylpyrrolidone, N-octylpyrrolidone, dimethylacetamide (DMAC), dimethylsulfoxide (DMSO), dimethylformamide (DMF), butyrolactone and mixtures of said solvents. In a particular embodiment, NMP is used as the solvent.

The dynamic viscosity of the polymer solution, measured according to DIN EN ISO 1628-1 at 22° C., usually is in the range of from 3,000 to 15,000 mPa·s, e.g., from 4,000 to 9,000 mPa·s, or even 4,900 to 5,900 mPa·s.

The center fluid or bore liquid which is used in step b) of the process of the present disclosure comprises at least one of the above-mentioned solvents and a precipitation medium chosen from the group of water, glycerol and other alcohols.

In certain embodiments, the center fluid additionally comprises a further additive to modify the surface of the membrane in order to further increase the performance of the membrane. In one embodiment of the invention, the amount of the additive in the center fluid is from 0.02 to 2 wt %, for example from 0.05 to 0.5 wt %, or from 0.05 to 0.25 wt %, related to the total weight of the center fluid.

Examples of suitable additives include hyaluronic acid and zwitterionic polymers as well as copolymers of a vinyl polymerizable monomer having a zwitterion in the molecule and another vinyl polymerizable monomer. Examples of zwitterionic (co)polymers include phosphobetains, sulfobetains, and carboxybetains.

The center fluid generally comprises 40-100 wt % precipitation medium and 0-60 wt % of solvent. In one embodiment of the process, the center fluid comprises 44-69 wt % precipitation medium and 31-56 wt % of solvent. In a particular embodiment, the center fluid comprises 49-63 wt % of water and 37-51 wt % of NMP. In another embodiment, the center fluid comprises 53-56 wt % of water and 44-47 wt % of NMP.

In one embodiment of the process, the polymer solution coming out through the outer slit opening of the spinneret is guided through a spinning shaft with controlled atmosphere. In one embodiment of the process, the spinning shaft is held at a temperature within the range of from 2 to 90° C., e.g., within the range of from 25 to 70° C., or from 30 to 60° C.

In one embodiment, the precipitating hollow fiber is exposed to a humid steam/air mixture comprising a solvent in a content of from 0 to 10 wt %, for instance, from 0 to 5 wt %, or from 0 to 3 wt %, related to the water content. The temperature of the humid steam/air mixture is at least 15° C., preferably at least 30° C., and at most 75° C., e.g. not higher than 62° C. Further, the relative humidity in the humid steam/air mixture is from 60 to 100%.

The effect of the solvent in the temperature-controlled steam atmosphere is to control the speed of precipitation of the fibers. When less solvent is employed, the outer surface will obtain a denser surface, and when more solvent is used, the outer surface will have a more open structure.

By controlling the amount of solvent within the temperature-controlled steam atmosphere surrounding the precipitating membrane, the amount and size of the pores on the outer surface of the membrane can be modified and controlled.

In one embodiment of the process of the present disclosure, the temperature of the spinneret is 50-70° C., e.g., 55-61° C., the temperature of the spinning shaft is 25-65° C., for instance, 50-60° C. The distance between the opening of the nozzle and the precipitation bath is from 30 to 110 cm, for instance, 45 to 55 cm. The precipitation bath has a temperature of 10-80° C., e.g. 20-40° C. In one embodiment, the spinning velocity is in the range of 15-100 m/min, for instance, 25-55 m/min.

In one embodiment of the invention, the precipitation bath comprises from 85 to 100 wt % of water and from 0 to 15 wt % of solvent, e.g., NMP. In another embodiment, the precipitation bath comprises from 90 to 100 wt % water and from 0 to 10 wt % NMP.

The hollow fiber membrane obtained by steps a) and b) is subsequently washed to remove waste components (step c). In one embodiment of the process, the hollow fiber membrane is passed through at least one water bath at a temperature in the range of from 70 to 90° C. In another embodiment, the membrane is passed through two water baths. In still another embodiment, the membrane is passed through five water baths. In certain embodiments of the process, the individual water baths have different temperatures. For instance, each water bath may have a higher temperature than the preceding water bath.

The membrane then is subjected to a two-stage drying and tempering treatment (step d) which comprises drying said membrane by applying a temperature in the range of from 210 to 280° C., e.g., 220 to 260° C., to the outer surface of the membrane for a time in the range of from 1 to 4 seconds, e.g., 2 to 3 seconds; and subsequently tempering said membrane by applying a temperature in the range of from 180 to 200° C. to the outer surface of the membrane for a time in the range of from 2 to 5 seconds, e.g., 3 to 4 seconds.

The hollow fiber membrane optionally is sterilized after dying. Suitable sterilization methods include treatment with steam, ethylene oxide, or radiation. In one embodiment of the process, the hollow fiber membrane is steam-sterilized at temperatures of at least 121° C. for at least 21 minutes.

In one embodiment, the membrane obtained by the process of the present disclosure comprises 80-99 wt % of polysulfone, polyethersulfone (PES), or polyarylethersulfone (PAES), optionally in combination with polyamide (PA); and 1-20 wt % of polyvinylpyrrolidone (PVP).

In one embodiment, the PVP comprised in the permselective hollow fiber membrane consists of a high (≥100 kDa) and a low (<100 kDa) molecular weight component and comprises 10-45 wt %, based on the total weight of PVP in the membrane, of a high molecular weight component, and 55-90 wt %, based on the total weight of PVP in the membrane, of a low molecular weight component.

In one embodiment, the hollow fiber membrane obtained by the process of the present disclosure has an inner diameter of from 180 to 250 μm. In another embodiment, the inner diameter is 185 to 195 μm. In still another embodiment, the inner diameter is 210 to 220 μm.

The wall thickness of the hollow fiber membrane usually is in the range of from 20 to 55 μm. In one embodiment, the wall thickness is 33 to 37 μm. In another embodiment, the wall thickness is 38 to 42 μm. In still another embodiment, the wall thickness is 43 to 47 μm. In yet another embodiment, the wall thickness is 48 to 52 μm.

The hollow fiber membrane obtained by the process of the present disclosure can have a symmetric wall structure or an asymmetric wall structure. In one embodiment, the membrane wall has a symmetric sponge structure. In another embodiment, the membrane wall has an asymmetric sponge structure. In yet another embodiment of the process, the membrane wall has an asymmetric wall structure and comprises a layer having a finger structure, i.e., featuring macrovoids having a size of more than 5 μm.

A further aspect of the present disclosure is a device capable of performing a continuous two-stage drying and tempering treatment of permselective hollow fiber membranes.

The device for continuously drying and tempering hollow fiber membranes 4 comprises a plurality of rollers 5 disposed within a housing 1. The housing 1 has an inlet 2 and an outlet 3 for the hollow fiber membranes 4 and an exhaust 7.

The rollers 5 are configured to heat the hollow fiber membranes 4. The hollow fiber membranes 4 are passed over the outer surface of the rollers 5, contacting the hot surface and being heated in the process. The outer surface of each roller 5 of the plurality of rollers 5 is heatable individually. In one embodiment, the outer surface of each roller (5) is configured to be heatable to a temperature in the range of from 150° C. to 300° C. The temperature of each roller 5 is controlled individually. Heating can be performed by various methods. For instance, the outer surface of the roller 5 can be heated electrically, i.e. by resistance heating or inductive heating, or it can be heated by radiation heating either from the inside of the roller 5 or from the outside of the roller 5, or both.

Each roller 5 is individually driven by a drive 6. The drive 6 usually will be a motor. The speed of each roller 5 is regulated individually. In one embodiment, each roller 5 is configured to rotate at a circumferential speed in the range of from 30 to 100 m/min, e.g., 45 to 75 m/min.

The rollers 5 are positioned within the housing 1 such that the axes of all rollers 5 are parallel and all axes lie in a single common plane. In one embodiment, the number of rollers 5 is 2 to 20, e.g., 5 to 10, for instance, 8 to 10. In one embodiment, the gap a between the first two rollers 5 downstream of the inlet 2 is in the range of 0.2 to 8 mm, for instance, 1 to 7 mm, e.g., 3 to 5 mm. In one embodiment, all rollers 5 in the device have the same diameter D. In one embodiment of the device, the diameter D is in the range of from 200 to 300 mm.

On their way through the device from the inlet 2 to the outlet 3, the hollow fibers 4 pass over the heated surfaces of the rollers 5 as shown in FIG. 1. For a device, with rollers of equal size, the length of each individual hollow fiber 4 in contact with the heated surface of the rollers 5 (the "contact length") approximately is (N−1)*π*D, wherein N is the number of rollers 5 in the device, and D is the Diameter of a roller 5. In one embodiment of the device, the contact length is at least 1 m. In another embodiment, the contact length is at least 2 m. In still another embodiment, the contact length is at least 6 m.

In one embodiment of the device, every other roller 5 of the plurality of rollers 5 is configured to be moveable to a position wherein its axis is outside the plane formed by the axes of the two adjacent rollers 5.

The housing 1 features an exhaust 7, which is connected to a fan 9. During operation of the device, the fan 9 removes water vapor generated by evaporating water from the hollow fiber membranes 4 from housing 1, thereby supporting the drying process. The throughput of the fan 9 is controlled by a controller 8. In one embodiment, the fan 9 is configured to have a throughput in the range of from 200 to 400 m$^3$ gas per hour.

In one embodiment of the device, the hosing 1 is configured to be separated into two compartments, each compartment comprising a part of the total number of rollers 5. In an illustrative example of the device, the total number of rollers is 10; the first compartment downstream the inlet 2 comprising 4 rollers 5 and the second compartment comprising 6 rollers 5.

Figure 2:
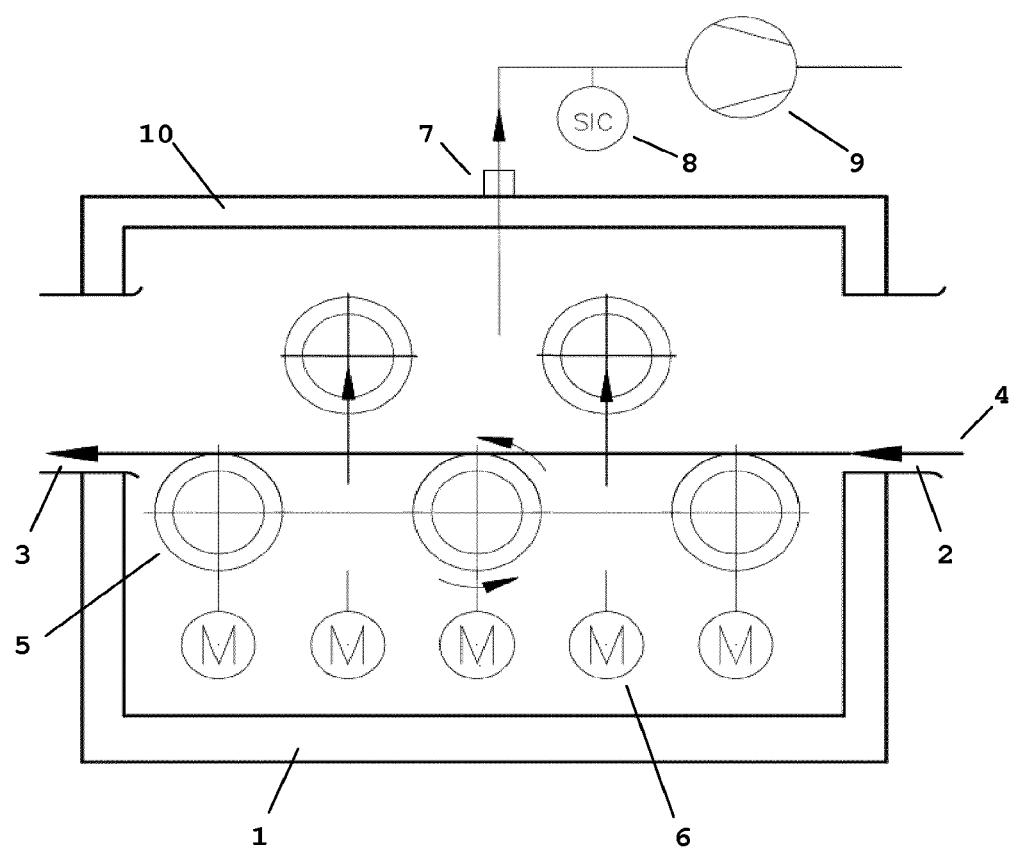
FIG. 2 shows as device in the "lay-on position" according to an embodiment of the present disclosure.

An illustrative embodiment of the device having five rollers 5 is shown in FIGS. 1 and 2. The device comprises a housing 1 having an inlet 2 and an outlet 3 for hollow fiber membranes 4. Five rollers 5 are disposed within the housing 1. Each roller 5 is driven individually by a motor 6. FIG. 1 shows the device during treatment of hollow fiber membranes 4 (in "working position"). The rollers 5 are positioned within the housing such that their centers are aligned. The minimum distance a between the first two rollers 5 is also shown. As illustrated by FIG. 1, the hollow fiber membranes 4 enter the device through inlet 2, pass over the surface of rollers 5 and leave the device through outlet 3. As shown in FIG. 2, every other roller 5 can be shifted perpendicular to the plane formed by the axes of the rollers 5 in the working position. The upper part 10 of the housing 1 also can be raised to provide additional space for the rollers 5 and facilitate access to the interior of the device. In the position shown in FIG. 2 (the "lay-on position"), hollow fibers 4 can be fed through the device in a straight line from inlet 2 to outlet 3, and on returning the device to the working position shown in FIG. 1, the hollow fiber membranes 4 are automatically guided over the surfaces of rollers 5. As a result, laying-on of the hollow fiber membranes 4 at the start of the production process or after rupture of individual hollow fiber membranes 4 during the production process is greatly facilitated. The housing 1 features an exhaust 7, which is connected to a fan 9. The throughput of the fan 9 is controlled by controller 8. In one embodiment of the device, the fan is configured to remove a gas volume of 200 to 400 m$^3$ per hour from the housing 1.

It will be understood that the features mentioned above and those described hereinafter can be used not only in the combination specified but also in other combinations or on their own, without departing from the scope of the present invention.

The present invention will now be described in more detail in the examples below. The examples are not intended to limit the scope of the present invention, but are merely an illustration of particular embodiments of the invention.

Analytical Methods i) Membrane Bundle Preparation

[A] Preparation of Hand Bundles:

The preparation of the membrane bundle after the spinning process is necessary to prepare the fiber bundle for the following performance tests. The first process step is to cut the fiber bundles to a defined length of 23 cm. The next process step consists of melting the ends of the fibers. An optical control ensures that all fibers are well melted. Then, the ends of the fiber bundle are transferred into a potting cap. The potting cap is fixed mechanically and a potting tube is put over the potting caps. Then the fibers are potted with polyurethane. After the polyurethane has hardened, the potted membrane bundle is cut to a defined length and stored dry before it is used for the different performance tests.

[B] Preparation of Mini-Modules:

Mini-modules [=fiber bundles in a housing] are prepared in a similar manner. The mini-modules ensure protection of the fibers and are used for steam-sterilization with residual water on the fiber. The manufacturing of the mini-modules differs in the following points:

⇨ The number of fibers required is calculated for an effective surface A of 360 cm² according to equation (1)

$$A = \pi \cdot d_i \cdot l \cdot n \, [\text{cm}^2] \quad (1)$$

with
 $d_i$=inner diameter of fiber [cm]
 n=amount of fibers
 l=effective fiber length [cm]
⇨ The fiber bundle is cut to a defined length of 20 cm
⇨ The fiber bundle is transferred into the housing before melting the fiber ends and performing the subsequent steps.

[C] Preparation of Filters:

The filter (=dialyzer) comprises about 8,000 to 10,000 fibers with an effective surface area of 1.4 m². A filter is characterized by a cylindrical housing with two connectors for the dialyzing fluid and caps applied on both ends, each with one centered blood connector. The manufacturing process (after winding) can be divided into the following main steps:

⇨ the cut bundles (length approx. 30 cm) are transferred into the housing with a special bundle claw;
⇨ both ends of the bundles are closed by a closing process
⇨ the fibers are potted into the housing with polyurethane (PUR);
⇨ the ends are cut to open the fibers;
⇨ the caps are welded to the blood connectors using ultrasonic welding;
⇨ final treatment comprises: rinsing, integrity testing, final drying
⇨ the filters are packed in sterile bags and steam sterilized.

ii) Hydraulic Permeability (Lp) of Hand Bundles and Mini-Modules

The hydraulic permeability of a membrane bundle is determined by pressing a defined volume of water under pressure through the membrane bundle, which has been sealed on one side, and measuring the required time. The hydraulic permeability can be calculated from the determined time t, the effective membrane surface area A, the applied pressure p and the volume of water pressed through the membrane V, according to equation (2):

$$Lp = V/[p \cdot A \cdot t] \quad (2)$$

From the number of fibers, the fiber length as well as the inner diameter of the fiber, the effective membrane surface area A is calculated. The membrane bundle has to be wetted thirty minutes before the Lp-test is performed. For this purpose, the membrane bundle is put in a box containing 500 ml of ultrapure water. After 30 minutes, the membrane bundle is transferred into the testing system. The testing system consists of a water bath that is maintained at 37° C. and a device where the membrane bundle can be mounted. The filling height of the water bath has to ensure that the membrane bundle is located underneath the water surface in the designated device. To avoid that a leakage of the membrane leads to a wrong test result, an integrity test of the membrane bundle and the test system has to be carried out in advance. The integrity test is performed by pressing air through the membrane bundle that is closed on one side of the bundle. Air bubbles indicate a leakage of the membrane bundle or the test device. It has to be checked if the leakage is due to an incorrect mounting of the membrane bundle in the test device or if a real membrane leakage is present. The membrane bundle has to be discarded if a leakage of the membrane is detected. The pressure applied in the integrity test has to be at least the same value as the pressure applied during the determination of the hydraulic permeability in order to ensure that no leakage can occur during the measurement of the hydraulic permeability because the pressure applied is too high.

iii) Selectivity/Sieving Coefficient (SC) for Proteins of Hand Bundles, Mini-Modules and Filters The selectivity of a membrane is determined by sieving coefficient measurements. For this purpose, the medium in which the protein (here myoglobin, MW=17 kDa; and albumin, MW=66 kDa) is dissolved is of crucial importance. The media used in this testing procedure is PBS buffer with a pH of 7.2. In general, the sieving coefficient of the particular molecule is obtained as follows: The particular protein solution is maintained at a temperature of 37° C.±1° C. and pumped under defined conditions (blood flow (Qs), TMP and filtration rate (UF)) through the testing device (hand bundles, mini-modules or filters). Then, the concentration of the protein in the feed (in), in the retentate (r) and in the filtrate (f) is determined and the sieving coefficient (SC) can then be calculated according to the following equation (3):

$$SC[\%] = 2 \cdot c(f)/[c(in) + c(r)] \cdot 100\% \quad (3)$$

If the concentration of the protein in the filtrate is zero, a sieving coefficient of 0% is obtained. If the concentration of the protein in the filtrate equals the concentration of the protein in the feed and the retentate, a sieving coefficient of 100% is obtained.

[A] Sieving Coefficient in Aqueous Solution on Hand Bundles and Mini-Modules

The Sieving Coefficient experiments in aqueous solution of myoglobin and albumin are performed using two different experimental set-ups with separate solutions. First, the sieving coefficient of myoglobin is determined. Then the sieving coefficient of albumin is determined.

The concentration of myoglobin in the PBS buffer is 100 mg/l. Prior to the Sieving Coefficient experiment, an Lp-test is performed as described above. The sieving coefficient experiment for myoglobin is run in single pass, the myoglobin solution being slowly stirred by a magnetic bar stirrer. Testing conditions are defined as follows:

The intrinsic flow rate ($J_v$ in cm/s) and wall shear rate ($\gamma$ in $s^{-1}$) are fixed whereas the blood flow ($Q_B$) and filtration rate (UF) is calculated using equations (4) and (5), respectively:

$$Q_B \text{ [ml/min]} = \gamma \cdot n \cdot \pi \cdot di^3 \cdot 60/32 \quad (4)$$

$$UF \text{[ml/min]} = J_V \cdot A \cdot 60 \quad (5)$$

with
n=amount of fibers
$d_i$=inner diameter of fiber [cm]
$\gamma$=shear rate [$s^{-1}$]
A=effective membrane surface [$cm^2$]
wherein A is calculated according to equation (1).

When testing a hand bundle or a mini-module, the shear rate is set to 500 $s^{-1}$ and the intrinsic flow rate is defined to be $0.38 \cdot 10^{-04}$ cm/s.

The first samples are taken after 15 minutes (pool, retentate, and filtrate) and a second time after 60 min. At the end, the test-bundle is rinsed for some minutes with PBS-buffer. Then the test is stopped.

Subsequently, the SC-test of albumin is performed. 60 g of albumin are dissolved in PBS-buffer and the experiment is run re-circulating, the albumin solution being slowly stirred by a magnetic bar stirrer. In the test set-up, the $Q_B$ is calculated according to equation (4), a fixed TMP of 400 mmHg is set and the UF as well as the retentate flow is a result of the test conditions and the membrane permeability properties. After 15 minutes, the flow is switched to single-pass and samples (pool, retentate, and filtrate) are taken. After the SC-test the test-bundle can be rinsed once more with PBS-buffer and used to perform a second Lp-test in order to get an indication of the adsorption capacity of the membrane for the protein.

EXAMPLES

The dynamic viscosity $\eta$ of the polymer solutions was determined according to DIN ISO 1628-1 at a temperature of 22° C. using a capillary viscosimeter (ViscoSystem® AVS 370, Schott-Geräte GmbH, Mainz, Germany).

Example 1

A polymer solution was prepared by dissolving polyethersulfone (Ultrason® 6020, BASF Aktiengesellschaft) and polyvinylpyrrolidone (K30 and K85, BASF Aktiengesellschaft) and distilled water in N-methylpyrrolidone (NMP). The weight fraction of the different components in the polymer spinning solution was: PES:PVP K85:PVP K30:$H_2O$:NMP=13.6:2.6:5:75.6. The viscosity of the polymer solution was 8,540 mPa·s.

To prepare the solution, NMP and water were first filled into a 30 L container with finger-paddle agitator. The PVP was added to the NMP and stirred at 50° C. until a homogeneous clear solution was obtained. Finally, the polyethersulfone was added. The mixture was stirred at 50° C. until a clear highly viscous solution was obtained. The warm solution was cooled to 20° C. and degassed for 1-2 hours at 50 mmHg. The highly viscous polymer solution was transferred to a stainless steel container.

A bore liquid was prepared by mixing distilled water and N-methylpyrrolidone (NMP). The weight fraction of the two components in the center fluid was: $H_2O$:NMP=53 wt %:47 wt %.

The preparation of the bore liquid was carried out as follows:
⇨ Distilled water was filled into a stainless steel container; NMP was added and the mixture was stirred for approximately 1 min;
⇨ The clear mixture was filtered into a second stainless steel container and degassed at 50 mmHg.

A membrane was formed by heating the polymer solution to 50° C. and passing the solution as well as the bore liquid through a spinning die. The temperature of the die was 55° C. and of the spinning shaft was 50° C. The hollow fiber membrane was formed at a spinning speed of 50 m/min. The liquid capillary leaving the die was passed into a water bath (ambient temperature). The distance between the die and the precipitation bath was 100 cm. The hollow fiber membrane formed was guided through 5 different water baths.

After leaving the fifth water bath, the fibers were fed to an online dryer having two compartments with heated rollers, compartment 1 comprising 4 heated rollers and compartment 2 comprising 6 heated rollers. The membranes were dried in the first compartment at a temperature in the range of from 220 to 280° C. (roller 1-4: 250/280/260/220° C.) and tempered in the second compartment at a temperature in the range of from 180 to 190° C. (roller 5-10: 190/190/190/180/180/180° C.). Residence time in the first compartment was 2.4 seconds, residence time in the second compartment was 3.2 seconds.

The dry hollow fiber membrane had an inner diameter of 190 μm and an outer diameter of 260 μm and a fully asymmetric membrane structure. The active separation layer of the membrane was at the inner side. The active separation layer is defined as the layer with the smallest pores. The membranes were wound on a winding wheel and mini-modules with 356 fibers were prepared according to the method described above.

Comparative Example 1

Example 1 was repeated. After leaving the fifth water bath, the fibers were wound on a winding wheel and cut into bundles. The bundles were rinsed with water at 70° C., spin-dried and subsequently dried at 50° C. in a drying cabinet.

The dry hollow fiber membrane had an inner diameter of 190 μm and an outer diameter of 260 μm and a fully asymmetric membrane structure. The active separation layer of the membrane was at the inner side. Mini-modules with 356 fibers were prepared according to the method described above.

Steam Sterilized Membranes (Mini-Modules):

The performance of the membranes produced in Example 1 and Comparative Example 1, respectively, was measured on steam-sterilized ((22±1) min, (121±1)° C.) mini-modules as described above. Hydraulic permeability as well as sieving coefficient of myoglobin and albumin in aqueous solution was tested. The results are shown in Table 1.

TABLE 1

Lp value, SC of myoglobin and albumin measured in aqueous solution.

| Membrane | Lp [$10^{-04}$ · cm/ bar · s] | Sieving coefficient in aqueous solution [%] | | SC (Myo)/ SC (Alb) | SC (Myo)- SC (Alb) |
| --- | --- | --- | --- | --- | --- |
| | | Myoglobin 17 kD 30' | Albumin 66 kD 30' | | |
| Example 1 | 35.9 ± 0.6 | 65.8 ± 1.4 | 4.5 ± 0.2 | 14.6 | 61.3 |
| Comparative Example 1 | 17.6 ± 2.2 | 45.0 ± 0.8 | 6 ± 1 | 9.0 | 39.0 |

It is apparent from the comparison that both the ratio of the sieving coefficients of myoglobin and albumin, and the difference of the sieving coefficients of myoglobin and albumin, which are indicators for the selectivity of the membrane, are much larger for the membrane of the invention.

The invention claimed is:

1. A device for continuously drying and tempering hollow fiber membranes comprising a plurality of rollers disposed within a housing, the housing having an inlet and an outlet for the hollow fiber membranes and an exhaust separate from the inlet and the outlet, wherein the device is configured to pass the hollow fiber membranes over an outer surface of the rollers while heating the hollow fiber membranes; the outer surface of each roller of the plurality of rollers being individually heatable and each roller being individually driven by a drive, and wherein the rollers are positioned within the housing such that the axes of all rollers are parallel and all axes lie in a single common plane,
    wherein the surface of each roller is configured to be heatable to a temperature in the range of from 150° C. to 300° C.,
    wherein each roller is configured to rotate at a circumferential speed in the range of from 30 to 100 m/min, and
    wherein the width of the gap between the first two rollers downstream of the inlet is in the range of 0.2 to 8 mm.

2. The device of claim 1, wherein the number of rollers is 2 to 20.

3. The device of claim 1, wherein the exhaust is connected to a fan which is configured to remove a gas volume of 200 to 400 m³ per hour from the housing, wherein the fan is positioned outside the housing.

4. The device of claim 1, wherein the number of rollers is at least 3; and every other roller of the plurality of rollers is configured to be moveable to a position wherein its axis is outside the plane formed by the axes of the two adjacent rollers.

5. The device of claim 1, wherein the housing is configured to be separated into two compartments, wherein each compartment comprising a portion of the plurality of rollers.

6. The device of claim 2, wherein the exhaust is connected to a fan which is configured to remove a gas volume of 200 to 400 m³ per hour from the housing, wherein the fan is positioned outside the housing.

7. The device of claim 2, wherein the number of rollers is at least 3; and every other roller of the plurality of rollers is configured to be moveable to a position wherein its axis is outside the plane formed by the axes of the two adjacent rollers.

8. The device of claim 3, wherein the number of rollers is at least 3; and every other roller of the plurality of rollers is configured to be moveable to a position wherein its axis is outside the plane formed by the axes of the two adjacent rollers.

9. The device of claim 2, wherein the housing is configured to be separated into two compartments, wherein each compartment comprising a portion of the plurality of rollers.

10. The device of claim 3, wherein the housing is configured to be separated into two compartments, wherein each compartment comprising a portion of the plurality of rollers.

11. The device of claim 4, wherein the housing is configured to be separated into two compartments, wherein each compartment comprising a portion of the plurality of rollers.

12. The device of claim 1, wherein for the plurality of rollers, each roller has the same diameter.

13. The device of claim 12, wherein the diameter is in the range of 200 mm to 300 mm.

14. The device of claim 1, wherein the outer surface of the rollers is configured to be heated electrically.

15. The device of claim 1, wherein the outer surface of the rollers is configured to be heated electrically via resistance heating.

16. The device of claim 1, wherein the outer surface of the rollers is configured to be heated electrically via inductive heating.

17. The device of claim 1, wherein the outer surface of the rollers is configured to be heated electrically via radiation heating.

* * * * *